(12) United States Patent
Sprenger

(10) Patent No.: US 8,771,674 B2
(45) Date of Patent: Jul. 8, 2014

(54) OLIGOSACCHARIDE COMPOSITION FOR TREATING SKIN DISEASES

(75) Inventor: Norbert Sprenger, Savigny (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/988,990

(22) PCT Filed: Nov. 21, 2011

(86) PCT No.: PCT/EP2011/070561
§ 371 (c)(1),
(2), (4) Date: May 22, 2013

(87) PCT Pub. No.: WO2012/076321
PCT Pub. Date: Jun. 14, 2012

(65) Prior Publication Data
US 2013/0251682 A1    Sep. 26, 2013

(30) Foreign Application Priority Data
Nov. 23, 2010 (EP) ..................... 10192227

(51) Int. Cl.
*A01N 63/00* (2006.01)
*C12N 5/00* (2006.01)

(52) U.S. Cl.
USPC ........................... 424/93.4; 435/325

(58) Field of Classification Search
USPC .......................................... 424/93.4; 435/325
See application file for complete search history.

(56) References Cited

U.S. PATENT DOCUMENTS 7,893,041 B2 *  2/2011  Morrow et al. ................. 514/62

OTHER PUBLICATIONS

Olivares et al. (Antimicrobial potential of four *Lactobacillus* strains isolated from breast milk. Journal of Applied Microbiology. (2006) 101:72-79).*

Ghaderi et al. (Effect of Breast-Feeding on the Development of Atopic Dermatitis. Iranian Journal of Allergy, Asthma and Immunology (2005) 4(3): 129-132).*

* cited by examiner

*Primary Examiner* — Karen Cochrane Carlson
*Assistant Examiner* — Natalie Moss
(74) *Attorney, Agent, or Firm* — K&L Gates LLP

(57) ABSTRACT

The invention discloses a composition comprising at least one N-acetyl-lactosamine, at least one sialylated oligosaccharide and at least one fucosylated oligosaccharide, for use in the prevention and/or treatment of skin conditions and skin diseases. Preferably said composition is a starter infant formula. Said skin disease is in particular atopic dermatitis.

13 Claims, 4 Drawing Sheets

FIGURE 1

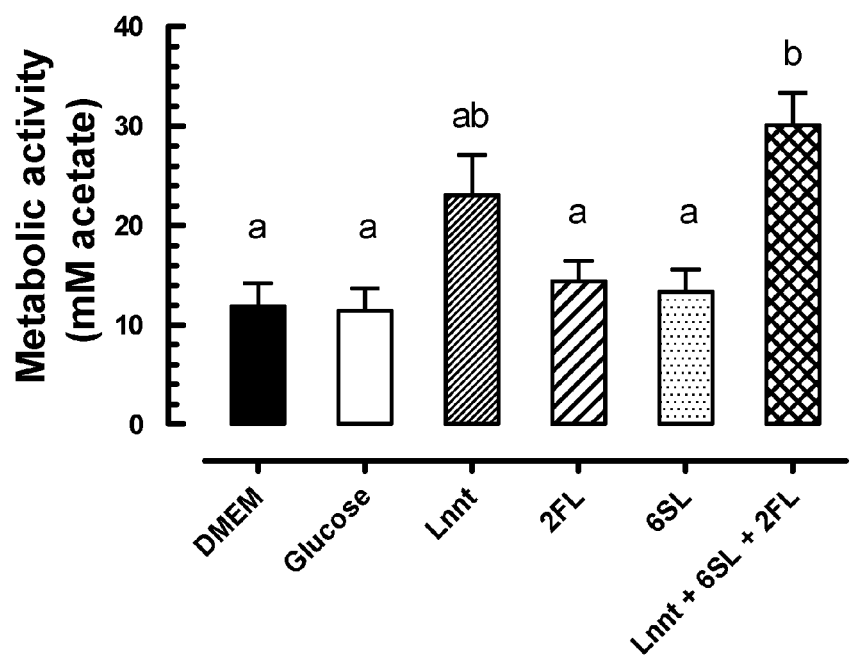

*Figure 1.* Experimental results showing metabolic stimulation of a bifidobacterium (B. longum subsp infantis) in DMEM culture medium either without additional carbohydrates or with additional glucose (Glc), or lacto-N-neoteraose (LNnT) or 2'fucosyllactose (2FL) or 6'sialyllactose (6SL) or a blend of LNnT, 6SL and 2FL. (n=6; mean with SEM are shown; significance by ANOVA indicated ($p<0.01$).

Note: Only the blend of LNnT, 6SL and 2FL stimulated significantly the production of acetate.

FIGURE 2

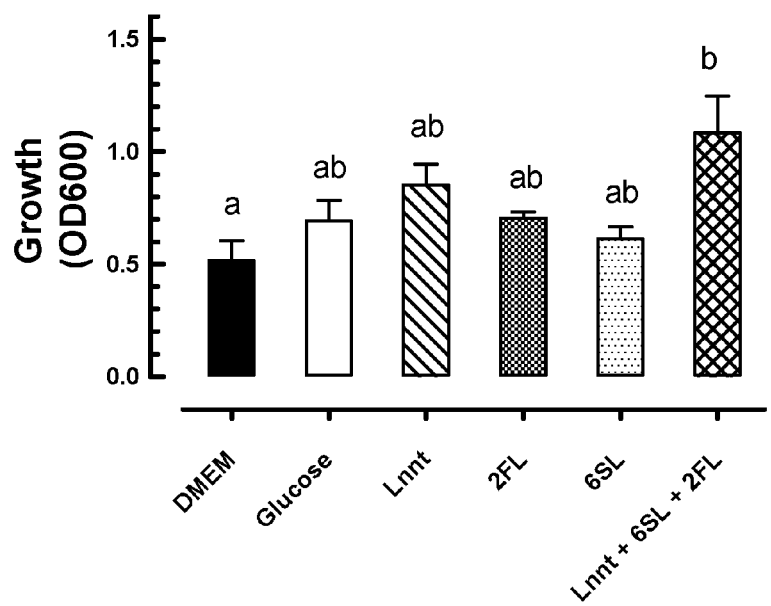

Figure 2. Experimental results showing in vitro growth of a bifidobacterium (B. longum subsp infantis) in culture medium either without additional carbohydrates or with additional glucose (Glc), or lacto-N-neoteraose (LNnT) or 2'fucosyllactose (2FL) or 6'sialyllactose (6SL) or a blend of LNnT, 6SL and 2FL.. (n=4; mean with SEM are shown; significance by ANOVA ($p<0.02$) indicated by small letters).

FIGURE 3

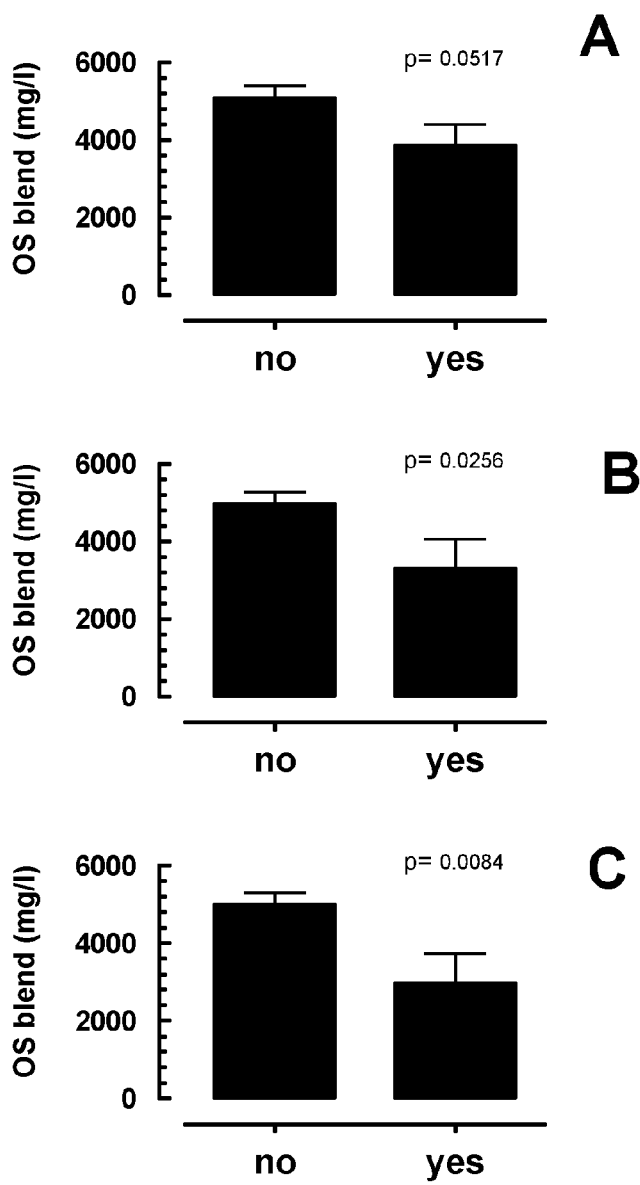

*Figure 3. Experimental results showing in caesarean born children absence (no) and occurrence (yes) of (A) allergic diseases, (B) atopic allergies, (C) atopic eczema up to 2 years of age. Plotted are amounts of a specific oligosaccharide blend measured in breast milk. Here the represented oligosaccharide blend is the sum of 2'fucosyllactose (2FL), Lacto-N-neotetraose (LNnT) and 6'siaylllactose (6SL). (Statistical significance is indicated)*

FIGURE 4

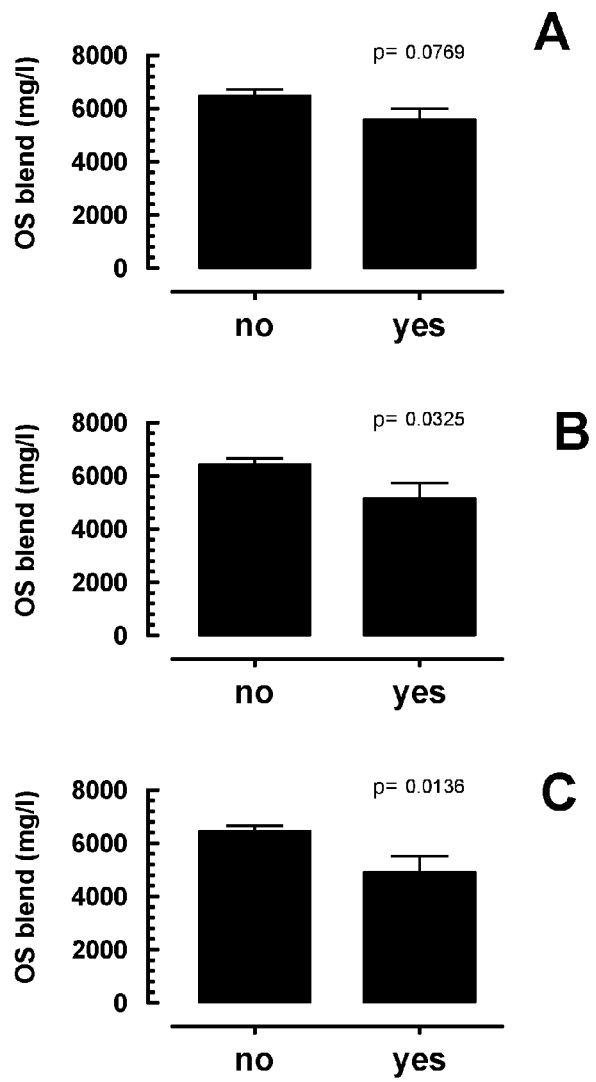

*Figure 4.* Experimental results showing in caesarean born children absence (no) and occurrence (yes) of (A) allergic diseases, (B) atopic allergies, (C) atopic eczema up to 2 years of age. Plotted are amounts of a specific oligosaccharide blend measured in breast milk. Here the represented oligosaccharide blend is the sum of 2'fucosyllactose (2'FL), Lacto-N-neotetraose (LNnT), Lacto-N-tetraose (LNT), 6'sialyllactose (6SL) and 3'siaylllactose (3SL). (Statistical significance is indicated)

OLIGOSACCHARIDE COMPOSITION FOR TREATING SKIN DISEASES

CROSS REFERENCE TO RELATED APPLICATIONS

The present application is a National Stage of International Application No. PCT/EP2011/070561, filed on Nov. 21, 2011, which claims priority to European Patent Application No. 10192227.6, filed Nov. 23, 2010, the entire contents of which are being incorporated herein by reference.

This invention relates to a composition for use in the prevention and/or treatment of skin conditions, such as the promotion of skin health, and skin diseases, particularly atopic dermatitis.

BACKGROUND OF THE INVENTION

Atopic dermatitis is a chronic itchy skin disease that is common in children but may occur at any age. It is also known as eczema or atopic eczema. There is a strong association between food allergy and atopic dermatitis in the age group of young children, and food allergies are often suspected in children with atopic dermatitis.

Atopic dermatitis usually occurs in people who have an atopic tendency. This means they may develop any or all of three closely linked conditions: atopic dermatitis, asthma and hay fever (allergic rhinitis).

A phenomenon of atopic dermatitis occurs as follows. Patches of sensitive skin flare up in a rash in response to certain triggers. These triggers vary from person to person. In the case of infants and young children, the list of common triggers to watch for includes cow's milk and other possible ingredients of infant formula such as wheat or soy. Atopic dermatitis can become a vicious cycle. Something irritates the child skin, making it red and inflamed. It itches, the child scratches it, and the skin becomes more inflamed. The outer protective layer of the skin is lost, and the affected area becomes even more sensitive to irritants and dries out easily. The infant continues to be exposed to whatever it was that triggered these episodes in the first place. The rash develops further and the cycle perpetuates itself.

There is no known single cause for atopic dermatitis. It probably reflects more than one condition. There are many theories regarding the underlying mechanisms. Current research is investigating the role of filaggrin gene mutations, defects in skin cells (keratinocytes), the immune system, skin surface microbes (bacteria, viruses and yeasts), and many other factors.

All skin conditions and skin diseases can affect the general population or the population of persons at risk of allergies or the population of allergic (hence sick) persons.

Such skin conditions and skin diseases, and in particular atopic dermatitis, are of particular importance for infants, babies or children as they have a sensitive skin that undergoes an intense growth and phases of multiplication, rendering it even more susceptible to skin diseases. The population of infants without history of allergies in their family, and who become allergic, is increasing.

Hypoallergenic foodstuff is a type of food which is unlikely to cause allergic reactions. Hypoallergenic foodstuffs have been developed, in particular for infant formulae, because infants and children are becoming increasingly likely to develop allergy in the first months/years of their life.

Hypoallergenic infant formulae are used to help, prevent and treat allergic diseases and particularly food allergies in infants and occasionally in young children. They are generally made without the use of common allergens like wheat, soy and dairy products. They also usually derive from cow's milk, however because of the way their proteins have been broken down, they are well tolerated by most infants.

Hypoallergenic infant formulae generally come in three main varieties: partially hydrolysed, extensively hydrolysed and free amino-acid-based. Hydrolyzed infant formulae have the larger protein chains broken down into shorter, easy to digest proteins, whereas free amino-acid formulae do not include protein chains at all, but rather contain all the basic amino acids. Partially hydrolysed infant formulae differ from extensively hydrolysed infant formulae in that their protein chains can be longer. Hypoallergenic infant formulae have the drawback that their cost is much higher than the cost of regular cow's milk formulae.

However, there is still a need for hypoallergenic infant formulae for the prevention and/or treatment of skin conditions and skin diseases that infant and even young children can develop, among which atopic dermatitis.

Human milk oligosaccharides (HMOs) are, collectively, the third largest solid constituents in human milk, after lactose and fat. HMO usually consists of lactose at the reducing end with a carbohydrate core that often contains a fucose or a sialic acid at the non-reducing end. There are approximately one hundred milk oligosaccharides that have been isolated and characterized, however these represent only a very small portion of the total number remaining to be characterized.

In the past, infant formulae were developed using HMO ingredients, such as fucosylated oligosaccharides, lacto-N-tetraose, lacto-N-neotetraose, or sialylated oligosaccharides, for different purposes.

EP 0 975 235 B1 from Abbott Laboratories describes a synthetic nutritional composition comprising one or more human milk oligosaccharides, wherein the HMOs in the composition are chosen among a group of eight HMOs (3-fucosyllactose, lacto-N-fucopentaose III, lacto-N-fucopentaose II, difucosyllactose, 2'-fucosyllactose, lacto-N-fucopentaose I, lacto-N-neotetraose and lacto-N-fucopentaose V) wherein said composition is intended for cases of normal, healthy infants, children, adults or individuals having specialized needs such as those that accompany certain pathological conditions. This European patent states that, generally speaking, oligosaccharides protect infants from viral and bacterial infections of the respiratory, gastrointestinal and uro-genital tracts. Nothing is mentioned concerning the issue of atopic dermatitis and more generally the prevention and/or treatment of skin disease.

From the foregoing, it may be seen that there is a need for an effective nutritional composition for the prevention of secondary atopic dermatitis or the promotion of skin health, particularly in infants and young children, and which may be conveniently and safely administered.

There is a need for an improvement of skin conditions or skin diseases, such as atopic dermatitis, by a non-drug-based intervention that is compatible with fragile individuals like infants or babies.

There is a need for a long term effect in the reduction of the frequency, occurrence, severity and/or duration of such skin conditions and skin diseases. There is furthermore a need for an effect that becomes measurable "later in life", especially some years after the intervention.

There is a need for a food intervention to infants, babies and children, targeted at risks of allergy or not, that induces a reduction of allergic manifestations, especially on the skin.

There is a need for such intervention that induces the maintenance or the improvement of skin health.

SUMMARY OF THE INVENTION

The present inventors have found surprisingly that the administration of a mixture of specific human oligosaccharides is particularly effective in the prevention and/or treatment of skin conditions and skin diseases, and in particular in the prevention and/or treatment of atopic dermatitis, and/or in the promotion of skin health.

Accordingly, the present invention provides a composition, comprising at least one N-acetyl lactosamine, at least one sialylated oligosaccharide and at least one fucosylated oligosaccharide, for use in the prevention and/or treatment of skin conditions and skin diseases, preferably atopic dermatitis.

The composition is preferably a synthetic nutritional composition. The composition comprises three different types of uses as synthetic nutritional composition. In the first case, individuals and particularly infants are healthy, without any risk of allergy because of no history of allergies in their family. In the second case, individuals and particularly infants are healthy, but at risk of allergy because of history of allergies in their family. In the third case, individuals and particularly infants are allergic, and hence sick. The first case is the preferred target according to the invention.

BRIEF DESCRIPTION OF THE SEVERAL VIEWS OF THE DRAWINGS

FIG. 1 illustrates a metabolic stimulation of a bifidobacterium (*B. longum* subsp *infantis*) in DMEM culture medium either without additional carbohydrates or with additional glucose (Glc), or lacto-N-neoteraose (LNnT) or 2'fucosyllactose (2FL) or 6'sialyllactose (6SL) or a blend of LNnT, 6SL and 2FL.

FIG. 2 illustrates in vitro growth of a bifidobacterium (*B. longum* subsp *infantis*) in culture medium either without additional carbohydrates or with additional glucose (Glc), or lacto-N-neoteraose (LNnT) or 2'fucosyllactose (2FL) or 6'sialyllactose (6SL) or a blend of LNnT, 6SL and 2FL.

FIG. 3 illustrates the experimental results showing in caesarean born children absence (no) and occurrence (yes) of (A) allergic diseases, (B) atopic allergies, (C) atopic eczema up to 2 years of age. Plotted are amounts of a specific oligosaccharide blend measured in breast milk.

FIG. 4 illustrates the experimental results showing in caesarean born children absence (no) and occurrence (yes) of (A) allergic diseases, (B) atopic allergies, (C) atopic eczema up to 2 years of age.

DETAILED DESCRIPTION OF THE INVENTION

As used herein, the following terms have the following meanings.

The term "infant" means a child under the age of 12 months.

The term "young child" means a child aged between one and three years.

The term "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The term "follow-on formula" means a foodstuff intended for particular nutritional use by infants aged over four months and constituting the principal liquid element in the progressively diversified diet of this category of person.

The term "starter infant formula" means a foodstuff intended for particular nutritional use by infants during the first four months of life.

The term "baby food" means a foodstuff intended for particular nutritional use by infants during the first years of life.

The term "infant cereal composition" means a foodstuff intended for particular nutritional use by infants during the first years of life.

The term "growing-up milk" means a milk-based beverage adapted for the specific nutritional needs of young children.

The term "weaning period" means the period during which the mother's milk is substituted by other food in the diet of an infant.

The term "skin disease" means atopic dermatitis and other related skin issues. Eczema is an atopic dermatitis.

The term "prevention and/or treatment of skin diseases" means the prevention and the reduction of frequency and/or occurrence and/or severity and/or duration of skin diseases, i.e. atopic dermatitis and other related skin issues, in particular atopic dermatitis. Occurrence is related to the number of any skin disease. Frequency is related to the number of the same skin disease. This prevention encompasses the reduction of frequency and/or of severity of said skin diseases later in life. The term "later in life" encompasses the effect after the termination of the intervention. The effect "later in life" can be preferably 2 to 4 weeks, 2 to 12 months or years (e.g. 2, 5, 10 years) after the termination of said intervention.

The term "skin conditions" means conditions that irritate, clog or inflame the skin. Skin conditions can cause symptoms of skin diseases such as redness, swelling, burning and itching.

The term "prevention and/or treatment of skin conditions" means the promotion of skin health and/or the prevention of skin dehydration and/or the enhancement of the hydration of the skin and/or the reduction of skin rash, roughness and/or dryness. This prevention further encompasses the establishment of a phenotype, visible or hidden, that accompany the reduction of frequency, occurrence, severity and/or duration of said skin conditions later in life.

The term "enhancement of the oral tolerance to allergens" means the reduction of the sensibility to allergens when taken orally.

The term "nutritional composition" means a composition which nourishes a subject. This nutritional composition is usually to be taken orally or intraveinously, and it usually includes a lipid or fat source and a protein source.

The term "synthetic mixture" means a mixture obtained by chemical and/or biological means, which can be chemically identical to the mixture naturally occurring in mammalian milks. A composition is said to be synthetic as soon as at least one of its components is obtained by chemical and/or biological (e.g. enzymatic) means.

The term "hypoallergenic nutritional composition" means a nutritional composition which is unlikely to cause allergic reactions.

The term "sialylated oligosaccharide" means an oligosaccharide having a sialic acid residue.

The term "fucosylated oligosaccharide" means an oligosaccharide having a fucose residue.

The term "prebiotic" means non-digestible carbohydrates that beneficially affect the host by selectively stimulating the growth and/or the activity of healthy bacteria such as *bifidobacteria* in the colon of humans (Gibson G R, Roberfroid M B. *Dietary modulation of the human colonic microbiota: introducing the concept of prebiotics. J. Nutr.* 1995; 125: 1401-12).

The term "probiotic" means microbial cell preparations or components of microbial cells with a beneficial effect on the health or well-being of the host. (Salminen S, Ouwehand A. Benno Y. et al. *"Probiotics: how should they be defined"* Trends Food Sci. Technol. 1999:10 107-10).

An "allergy" is an allergy which has been detected by a medical doctor and which can be treated occasionally or in a more durable manner.

All percentages are by weight unless otherwise stated.

The composition according to the invention is preferably a hypoallergenic composition.

Said composition contains at least one N-acetyl-lactosamine. That is to say that the composition according to the invention contains N-acetyl-lactosamine and/or an oligosaccharide containing N-acetyl-lactosamine. Suitable oligosaccharides containing N-acetyl-lactosamine include lacto-N-tetraose (LNT) and lacto-N-neotetraose (LNnT).

Thus, according to the invention, the N-acetyl-lactosamine is preferably selected from the group comprising lacto-N-tetraose (LNT) and lacto-N-neotetraose (LNnT).

LNT and LNnT may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

Preferably the composition according to the invention contains from 0.1 to 3 g N-acetyl-lactosamine per 100 g of composition on a dry weight basis.

According to the invention, the sialylated oligosaccharide is selected from the group comprising 3'-sialyllactose and 6'-sialyllactose. Preferably, both 3'-sialyllactose and 6'-sialyllactose are present in said composition. In this embodiment, the ratio between 3'-sialyllactose and 6'-sialyllactose lies preferably in the range between 5:1 and 1:2.

The 3'- and 6'-forms of sialyllactose may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetyl-neuraminic acid (sialic acid). Sialyllactoses are also commercially available for example from Kyowa Hakko Kogyo of Japan.

Preferably the composition according to the invention contains from 0.05 to 2 g, more preferably 0.1 to 2 g, of sialylated oligosaccharide(s) per 100 g of composition on a dry weight basis.

The fucosylated oligosaccharide may be selected from the group comprising 2'-fucosyllactose, 3-fucosyllactose, difucosyllactose, lacto-N-fucopentaoses (that is to say lacto-N-fucopentaose I, lacto-N-fucopentaose II, lacto-N-fucopentaose III and lacto-N-fucopentaose V), lacto-N-difucohexaose I, fucosyllacto-N-hexaose, Difucosyllacto-N-hexaose I and Difucosyllacto-N-neohexaose II. A particularly preferred fucosylated oligosaccharide is 2'-fucosyllactose (2-FL).

The fucosylated oligosaccharide may be isolated by chromatography or filtration technology from a natural source such as animal milks. Alternatively, it may be produced by biotechnological means using specific fucosyltransferases and/or fucosidase either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa Hakko Kogyo of Japan.

Preferably, the composition according to the invention contains from 0.1 to 3 g of fucosylated oligosaccharide(s) per 100 g of composition on a dry weight basis.

In a preferred embodiment, the composition of the invention comprises from 0.05 to 3 g of the total amount of N-acetylated lactosamine(s), sialylated oligosaccharide(s) and fucosylated oligosaccharide(s) per 100 g of composition.

The composition of the invention can further comprise at least one probiotic bacterial strain, said probiotic bacterial strain preferably being *Bifidobacteria* and/or *Lactobacilli*.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM I-2116, *Lactobacillus* reuteri sold by BioGaia A.B under the trademark Reuteri, *Lactobacillus johnsonii* CNCM I-1225, *Streptococcus salivarius* DSM 13084 sold by BLIS Technologies Limited of New Zealand under the designation K12, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

Preferably, the composition according to the invention contains from 10e3 to 10e12 cfu of probiotic bacterial strain, more preferably between 10e7 and 10e12 cfu, per g of composition on a dry weight basis.

The composition of the invention can further comprise at least one prebiotic, usually in an amount between 0.3 and 10% by weight of composition.

Prebiotics are usually non-digestible in the sense that they are not broken down and absorbed in the stomach or small intestine and thus remain intact when they pass into the colon where they are selectively fermented by the beneficial bacteria. Examples of prebiotics include certain oligosaccharides, such a fructooligosaccharides (FOS) and galactooligosaccharides (GOS). A combination of prebiotics may be used such as 90% GOS with 10% short chain fructo-oligosaccharides such as in the product by BENEO-Orafti sold under the trademark "Orafti® oligofructose" (see http://www.beneo-orafti.com/Our-Products/Oligofructose) (previously Raftilose®) or 10% inulin such as in the product sold by BENEO-Orafti under the trademark "Orafti® inulin" (see http://www.beneo-orafti.com/Our-Products/Inulin) (previously Raftiline®). A particularly preferred combination of prebiotics is 70% short chain fructo-oligosaccharides and 30% inulin, which is a product sold by BENEO-Orafti under the trademark "Prebio 1".

The composition according to the invention can further comprise other nutritional compounds that synergize with the claimed oligosaccharides to deliver the claimed benefits on skin, such as skin allergies or atopic dermatitis. Such additional compounds can be for example low allergenic proteins (i.e. hydrolyzed or partly hydrolyzed proteins), low lactose ingredients or low lactose saccharides. It is postulated that the synergy of the ingredients may be established by the fact that the ingredients all together help to maintain a low physiological level of an effector that stays below therehold where skin effects (such as atopic dermatitis) starts to show.

The composition according to the invention is preferably a synthetic nutritional composition. In this case, it can be a starter infant formula, an infant formula, a baby food, an infant cereal composition, a follow-on formula or a growing-up milk, and said composition is preferably a starter infant formula.

According to a preferred embodiment, the composition according to the invention is for use in healthy infants and healthy young children.

The composition according to the invention can be for use before and/or during a weaning period.

Thus preferably the composition according to the invention is for use in the reduction of frequency and/or occurrence and/or severity and/or duration of atopic dermatitis and/or for use in the promotion of skin health.

In an implementation, the composition according to the invention is for use in the promotion of skin health and/or for the prevention of skin dehydration and/or for use in the enhancement of the hydration of the skin and/or for use in the reduction of skin rash, roughness and dryness and/or for use in the enhancement of the oral tolerance to allergens.

The invention includes also the use of a composition comprising at least one N-acetyl lactosamine, at least one sialylated oligosaccharide and at least one fucosylated oligosaccharide, as a synthetic nutritional agent, for the prevention and/or treatment of skin conditions and skin diseases, preferably atopic dermatitis.

The invention includes also the use of a composition comprising at least one N-acetyl lactosamine, at least one sialylated oligosaccharide and at least one fucosylated oligosaccharide, as a synthetic nutritional agent, for enhancement of the oral tolerance to allergens.

These uses encompass the case where the composition is a supplement, preferably provided in the form of unit doses.

All the uses stated above are particularly intended for infants and young children. The compositions and uses as per the present invention are particularly suited for infants and children at risk of allergies, having a family history of allergies, or having already experienced some episodes of allergies (especially respiratory allergies or skin allergies). In one embodiment the composition and uses of the invention apply to teenagers or adults at risk of allergies or having experiences episodes of allergies (especially respiratory allergies or skin allergies).

Without wishing to be bound by theory, the inventors believe that the efficacy of the combination of oligosaccharides described above in the prevention and/or treatment of skin conditions and skin diseases, particularly atopic dermatitis, may be the result of the synergistic combination of mucosal immunity modulator effects triggered by lactic acid bacteria through their stimulation with a specific oligosaccharide blend. The inventors believe the establishment of mucosa associated microbiota at large with minimal inflammatory stimulation is achieved by the selective promotion of beneficial commensal lactic acid bacteria with simultaneous modulation of inflammatory regulators such as galectins (e.g. Galectin-1 and galectin-3). Moreover, such composition may modulate the metabolism of endogenous microbiota leading to production of short-chain fatty acid that will contribute to activate immune cells underlying the gut mucosa. Following triggering of the mucosal immune system, activated immune cells, immune-active compounds and/or immune mediators will circulate to distal locations, including skin, where they will exert immune modulatory activity. All together, these mechanisms will contribute to balance potential skin inflammatory conditions leading to improvement of related clinical manifestations such as dermatitis and eczema. Further, the inventors believe that such orchestrated immunity translates in lower skin sensitivity towards exogenous irritants and better skin barrier function leading to lower skin rash, roughness, and dryness, associated with reactive skin.

The oligosaccharides may be administered in the same composition or may be administered sequentially.

If the age group of 0 to 12 months of life is to be addressed, the composition is preferably a nutritional composition consumed in liquid form. It may be a nutritionally complete formula such as an infant formula, a follow-on formula or a growing-up milk.

Alternatively for the group of young children group, the composition may be a juice drink or other chilled or shelf stable beverage or a soup, for example, or a baby food, or an infant cereal composition.

The composition according to the invention also contains a protein source, preferably in an amount below 2.0 g per 100 kcal, even more preferably in an amount below 1.8 g per 100 kcal. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

The composition according to the present invention generally contains a carbohydrate source. This is particularly preferable in the case where the nutritional composition of the invention is an infant formula. In this case, any carbohydrate source conventionally found in infant formulae such as lactose, saccharose, maltodextrin, starch and mixtures thereof may be used although the preferred source of carbohydrates is lactose.

The composition according to the present invention generally contains a source of lipids. This is particularly relevant if the nutritional composition of the invention is an infant formula. In this case, the lipid source may be any lipid or fat which is suitable for use in infant formulae. Preferred fat sources include palm oleic, high oleic sunflower oil and high oleic safflower oil. The essential fatty acids linoleic and α-linolenic acid may also be added as may small amounts of oils containing high quantities of preformed arachidonic acid and docosahexaenoic acid such as fish oils or microbial oils. The fat source preferably has a ratio of n-6 to n-3 fatty acids of about 5:1 to about 15:1; for example about 8:1 to about 10:1.

The composition of the invention also contains preferably all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the composition of the invention may contain emulsifiers and stabilisers such as soy, lecithin, citric acid esters of mono- and di-glycerides, and the like.

The composition of the invention may also contain other substances which may have a beneficial effect such as lactoferrin, nucleotides, nucleosides, and the like.

A composition according to the invention will now be described by way of example.

The formula may be prepared in any suitable manner. For example, it may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The N-acetyl-lactosamine(s), sialylated oligosaccharide(s) and fucosylated oligosaccharide(s) will be added at this stage if the final product is to have a liquid form. If the final product is to be a powder, the oligosaccharides may likewise be added at this stage if desired. The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

The homogenised mixture is transferred to a suitable drying apparatus such as a spray dryer or freeze dryer and converted to powder. The powder should have a moisture content of less than about 5% by weight. The N-acetyl-lactosamine(s), sialylated oligosaccharide(s) and fucosylated oligosaccharide(s) may be added at this stage by dry-mixing along with the probiotic bacterial strain(s) if used, or by blending them in a syrup form of crystals, along with the probiotic bacterial strain(s) if used, and spray-dry (or freeze-dry).

If a liquid composition is preferred, the homogenised mixture may be sterilised then aseptically filled into suitable containers or may be first filled into the containers and then retorted.

In another embodiment, the composition of the invention may be a supplement including the N-acetyl-lactosamine(s), sialylated oligosaccharide(s) and fucosylated oligosaccharide(s) in an amount sufficient to achieve the desired effect in an individual. This form of administration is more suited to older children and adults. Preferably the daily dose of the N-acetyl-lactosamine(s) is from 0.1 to 3 g, the daily dose of the sialylated oligosaccharide(s) is from 0.1 to 2 g, and the daily dose of the fucosylated oligosaccharide(s) is from 0.1 to 3 g.

The amount of oligosaccharides to be included in the supplement will be selected according to the manner in which the supplement is to be administered. For example, if the supplement is to be administered twice a day, each supplement may contain 0.05 to 1.5 g of N-acetyl-lactosamine, 0.05 to 1 g of sialylated oligosaccharide and 0.05 to 1.5 g of fucosylated oligosaccharide.

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

An example of the composition of an infant formula according to the present invention is given below. This composition is given by way of illustration only. Another example is based on commercial NAN and/or lactogen Infant formulae (from Nestlé, Switzerland) to which the specific oligosaccharides of the invention are added as in the amount stated below.

| Nutrient | per 100 kcal | per liter |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic (70% FOS, 30% insulin) (g) | 0.64 | 4.3 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |

-continued

| Nutrient | per 100 kcal | per liter |
|---|---|---|
| P (mg) | 31 | 210 |
| Mg (mg) | 7 | 50 |
| Mn (μg) | 8 | 50 |
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| 3' sialyllactose (mg) | 30 | 200 |
| 6' sialyllactose (mg) | 6 | 40 |
| LNnT (mg) | 30 | 200 |
| 2FL (g) | 0.3 | 2.0 |

Experimental Data:
Finding Summary

The findings outlined below show that a specific blend of oligosaccharides promotes the metabolic activity and growth of lactic acid bacteria, such as *Bifidobacterium longum* subsp *infantis*. Without wishing to be bound by theory, this effect might in part explain the observation that relatively low amounts of such specific oligosaccharide blends were found in early milk of mothers, whose cesarean born children developed atopic allergies and especially atopic eczema up to the age of 2 years. This indicates that, according to the invention, providing a nutritional composition with a secured level of the specific oligosaccharides blend may help reestablishing the natural balance of bacteria in the intestinal tract of infants and/or thus positively influence the health status in regards to the prevention and/or treatment of skin conditions and skin diseases, preferably atopic dermatitis Study Model 1: Stimulation of *Bifidobacterium longum* Subsp *infantis*
Approach:

*Bifidobacterium longum* subsp *infantis* (ATCC15697) was grown anaerobic in API growth medium supplemented either with 1% (w/v) glucose, or 1% (w/v) 2'fucosyllactose (2FL) or 1% (w/v) lacto-N-neotetrasose (LNnT) or 1% (w/v) 6'sialyllactose (6SL) or 1% (w/v) of a combination of equal amounts of 2FL, LNnT and 6SL. Each overnight culture was diluted to have a starting OD600 of 0.1 in DMEM (Dulbeccos modified Eagle Medium) containing as a carbon source 0.1% glucose. This medium was used without any further carbohydrate supplement or with additional 1% (w/v) glucose, or 1% (w/v) 2'fucosyllactose (2FL) or 1% (w/v) lacto-N-neotetrasose (LNnT) or 1% (w/v) 6'sialyllactose (6SL) or 1% (w/v) of a combination of equal amounts of 2FL, LNnT and 6SL. Conditioning of DMEM media was thus done at 37° C. anaerobic.

After another over night incubation, growth of bacteria was monitored by measuring OD at 600 nm. Conditioned media were then centrifuged and supernatants filtered through a 0.22 micrometer filter to remove bacteria. Acetate in conditioned media was quantified by HPLC using a Hi-Plex H column and a UV detector.

Results:

We surprisingly found that an oligosaccharide blend composed of equal parts of a fucoslylated oligosaccharide (e.g. 2'FL), an N-acetylated oligosaccharide (e.g. LNnT) and a sialylated oligosaccharide (e.g. 6SL) significantly increased metabolic activity of a lactic acid bacterium (e.g. *bifidobacterium*), as seen by the formation of acetate (FIG. 1).

The oligosaccharide blend also stimulated growth of the bacterium (FIG. 2).

FIG. 1 illustrates the experimental results indicating a metabolic stimulation of a *bifidobacterium* (*B. longum* subsp *infantis*) in DMEM culture medium either without additional carbohydrates or with additional glucose (Glc), or lacto-N-neoteraose (LNnT) or 2'fucosyllactose (2FL) or 6'sialyllactose (6SL) or a blend of LNnT, 6SL and 2FL. (n=6; mean with SEM are shown; significance by ANOVA indicated (p<0.01). Note: Only the blend of LNnT, 6SL and 2FL stimulated significantly the production of acetate.

FIG. 2 illustrates the experimental results showing in vitro growth of a *bifidobacterium* (*B. longum* subsp *infantis*) in culture medium either without additional carbohydrates or with additional glucose (Glc), or lacto-N-neoteraose (LNnT) or 2'fucosyllactose (2FL) or 6'sialyllactose (6SL) or a blend of LNnT, 6SL and 2FL. (n=4; mean with SEM are shown; significance by ANOVA (p<0.02) indicated by small letters).

Study Model 2: Retrospective Epidemiologic Analysis of Breast Milk Samples and Occurrence of Allergic Diseases Up to the Age of 2 Years
Approach:

From a cohort of about 52 cesarean born infant mother pairs we analysed early milk samples for amounts of specific oligosaccharides present. To this end defatted milk samples were diluted 10 to 100 times in water and analysed by HPAEC (Dionex) equipped with a CarboPac PA1 column (Dionex) and an electrochemical detector. Oligosaccharide identification and quantification was done with authentic oligosaccharide standards. We plotted absence or presence of (A) allergic diseases, (B) atopic allergies, (C) atopic eczema for infants against amounts of an oligosaccharide blend composed of 2FL, LNnT, and 6SL (FIG. 3) or composed of 2FL, LNnT, LNT (lacto-N-tetraose), 6SL and 3SL (3'sialyllactose) (FIG. 4).

FIG. 3 illustrates the experimental results showing in caesarean born children absence (no) and occurrence (yes) of (A) allergic diseases, (B) atopic allergies, (C) atopic eczema up to 2 years of age. Plotted are amounts of a specific oligosaccharide blend measured in breast milk. Here the represented oligosaccharide blend is the sum of 2'fucosyllactose (2FL), Lacto-N-neotetraose (LNnT) and 6'siayllactose (6SL). (Statistical significance is indicated)

FIG. 4 illustrates the experimental results showing in caesarean born children absence (no) and occurrence (yes) of (A) allergic diseases, (B) atopic allergies, (C) atopic eczema up to 2 years of age. Plotted are amounts of a specific oligosaccharide blend measured in breast milk. Here the represented oligosaccharide blend is the sum of 2'fucosyllactose (2FL), Lacto-N-neotetraose (LNnT), Lacto-N-tetraose (LNT), 6'sialyllactose (6SL) and 3'siayllactose (3SL). (Statistical significance is indicated)

Results:

We surprisingly found a trend to relatively low levels of specific oligosaccharide blends in early milk when children developed an allergic disease (FIG. 3A, 4A). For atopic diseases and especially atopic eczema we measured significantly lower levels of the oligosaccharide blends in early milk of mothers whose children developed such allergies until the age of 2 years.

The invention claimed is:

1. A method for the prevention and/or treatment of skin conditions and skin diseases comprising the step of administering a composition comprising at least one chemically synthesized N-acetyl-lactosamine, at least one sialylated oligosaccharide and at least one fucosylated oligosaccharide to an individual in need of same, the sialylated oligosaccharide comprising 3'-sialyllactose and 6'-sialyllactose, and a ratio of 3'-sialyllactose to 6'-sialyllactose being in the range between 5:1 and 1:2 on a weight basis.

2. The method according to claim 1, wherein the N-acetyl-lactosamine is selected from the group consisting of lacto-N-tetraose and lacto-N-neotetraose.

3. The method according to claim 1, wherein the fucosylated oligosaccharide is selected from the group consisting of 2'-fucosyllactose, 3-fucosyllactose, difucosyllactose, lacto-N-fucopentaoses, lacto-N-difucohexaose I, fucosyllacto-N-hexaose, Difucosyllacto-N-hexaose I and Difucosyllacto-N-neohexaose II.

4. The method according to claim 1, wherein the composition comprises at least one probiotic bacterial strain.

5. The method according to claim 1, wherein the composition comprises at least one prebiotic.

6. The method according to claim 1, the composition is selected from the group consisting of a starter infant formula, an infant formula, a follow-on formula, a baby food formula, an infant cereals formula and a growing-up milk.

7. The method according to claim 1, wherein the individual is a healthy infants and healthy young children.

8. The method according to claim 1, wherein the composition is administered before and/or during a weaning period.

9. The method according to claim 1, wherein the individual has experienced at least one episode of the skin diseases.

10. The method according to claim 1, wherein the individual has experienced at least one episode of skin dehydration and/or skin rash, roughness and/or dryness.

11. The method according to claim 1, wherein the individual has experienced at least one episode of atopic dermatitis.

12. A method for the enhancement of the oral tolerance to allergens in an individual comprising the step of administering to the individual a composition comprising at least one N-acetyl lactosamine, at least one sialylated oligosaccharide and at least one fucosylated oligosaccharide, as a synthetic nutritional agent, the sialylated oligosaccharide comprising 3'-sialyllactose and 6'-sialyllactose, and a ratio of 3'-sialyllactose to 6'-sialyllactose being in the range between 5:1 and 1:2 on a weight basis.

13. The method according to claim 11, wherein the composition is a supplement.

* * * * *